United States Patent
Skinner

(10) Patent No.: US 6,288,255 B1
(45) Date of Patent: *Sep. 11, 2001

(54) ORGANOMETALLIC COMPOSITIONS

(75) Inventor: Christopher John Skinner, Brussels (BE)

(73) Assignee: Imperial Chemical Industries PLC, London (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/456,583

(22) Filed: Dec. 8, 1999

Related U.S. Application Data

(63) Continuation of application No. PCT/GB99/01982, filed on Jun. 24, 1999.

(30) Foreign Application Priority Data

Jul. 11, 1998 (GB) .................................................... 9815029

(51) Int. Cl.$^7$ ................................. C07F 7/00; C09K 3/00
(52) U.S. Cl. ................ 556/55; 252/182.11; 252/182.28; 252/182.33
(58) Field of Search .................... 252/182.11, 182.28, 252/182.33; 556/55

(56) References Cited

U.S. PATENT DOCUMENTS

| | | | |
|---|---|---|---|
| 4,927,884 | 5/1990 | Iwasawa et al. | 525/195 |
| 5,286,774 | 2/1994 | McGibbon et al. | 524/398 |
| 5,454,861 | 10/1995 | Hasegawa et al. | 106/2 |
| 5,716,745 | 2/1998 | Minemura et al. | 430/64 |
| 5,846,679 | 12/1998 | Kitahara et al. | 430/65 |

FOREIGN PATENT DOCUMENTS

| | | |
|---|---|---|
| 0 155 036 | 9/1985 | (EP) . |
| 0 688 837 | 12/1995 | (EP) . |
| 0516361B1 | 2/1996 | (EP) . |
| 2747675 | 10/1977 | (FR) . |
| 2 727 675 | 10/1997 | (FR) . |
| 1444933 | 8/1976 | (GB) . |
| 68-000620 | 6/1964 | (JP) . |
| 53-111017 | 9/1978 | (JP) . |
| 57-090014 | 6/1982 | (JP) . |
| 4-103668 | 4/1992 | (JP) . |
| 9-022134 | 1/1997 | (JP) . |
| 9717388 | 5/1997 | (WO) . |

OTHER PUBLICATIONS

Qui et al., Chemical Abstracts, vol. 117, abstract No. 69996, 1992.*

* cited by examiner

Primary Examiner—Porfirio Nazario-Gonzalez
(74) Attorney, Agent, or Firm—Pillsbury Winthrop LLP

(57) ABSTRACT

An organometallic composition comprises a complex of at least one metal selected from the group consisting of titanium, zirconium and hafnium and an acetoacetate ester in which the molar ratio of Ti or Hf to acetoacetate ester is in the range 1:2.5 to 1:10 or the molar ratio of Zr to acetoacetate ester is in the range 1:4.5 to 1:10 and said acetoacetate ester is an ester of an alcohol containing 1 to 6 carbon atoms. The organometallic composition is useful in polyisocyanate compositions, particularly those used as binders for lignocellulosic materials, and polyisocyanate compositions containing the organometallic compositions of the invention have good stability on storage.

11 Claims, No Drawings

ORGANOMETALLIC COMPOSITIONS

This is a continuation application under 35 U.S.C. Section 120 of International application Serial Number PCT/GB99/01982 filed on Jun. 24, 1999 which application designates the US.

This invention relates to organometallic compositions based on Group IVB metals and which are useful in polyisocyanate compositions especially compositions for binding lignocellulosic material.

The use of organic polyisocyanates as binders for lignocellulosic material in the manufacture of sheets or moulded bodies such as waferboard, chipboard, fibreboard and plywood is well known. In a typical process the organic polyisocyanate, optionally in the form of a solution, dispersion or aqueous emulsion, is applied to the lignocellulosic material which is then subjected to heat and pressure.

One suitable polyisocyanate composition is disclosed in PCT Application WO 97/17388. This composition comprises a Group IVB metal compound, preferably a titanium chelate, optionally in combination with a compatibilising compound and/or conventional release agents. Although these compositions perform well as binders for lignocellulosic material and provide good release performance, it is desirable to develop a more economical composition which provides improved stability on storage before use, together with good curing properties and excellent bonding strength when applied to the lignocellulosic material.

It has now been surprisingly found that certain compounds of Group IVB metals and acetoacetate esters can be used to cure polyisocyanate compositions and these compositions are very stable on prolonged storage and economical when used for binding lignocellulosic material.

According to the invention, an organometallic composition comprises a complex of at least one metal selected from the group consisting of titanium, zirconium and hafnium and an acetoacetate ester in which the molar ratio of Ti or Hf to acetoacetate ester is in the range 1:2.5 to 1:10 or the molar ratio of Zr to acetoacetate ester is in the range 1:4.5 to 1:10 and said acetoacetate ester is an ester of an alcohol containing 1 to 6 carbon atoms.

The titanium, zirconium or hafnium composition of the invention is described herein as a "complex". It is believed that some of the acetoacetate ester will be chemically bound to the metal (Ti, Zr or Hf) but some can be described as "free" ester. The exact proportions which are bound and free will depend partly upon the exact molar ratios present in the complex and which metal, or metals, are used, but it has been shown that the "free" ester does influence the properties, particularly the stability on storage of polyisocyanate compositions containing the complexes.

The molar ratio of titanium or hafnium to acetoacetate ester in the complex is in the range 1:2.5 to 1:10. When the metal is titanium, the molar ratio is preferably in the range 1:2.5 to 1:8 and more preferably in the range 1:3 to 1:6. Particularly preferred compounds have a molar ration in the range 1:4 to 1:6. In agreement with conventional theories about the co-ordination chemistry of titanium, it is believed that two molecules of acetoacetate ester will be chemically bound to a titanium atom and the remainder will be "free". When the metal is hafnium, the molar ratio is preferably 1:4.5 to 1:10 and more preferably 1:4.5 to 1:8, hafnium to acetoacetate ester. When the metal is zirconium, the molar ratio is from 1:4.5 to 1:10 and preferably from 1:4.5 to 1:8, zirconium to acetoacetate ester. For hafnium or zirconium, again in accordance with conventional theory, it is believed that, for complexes which contain 4 or more moles of acetoacetate ester, 4 molecules of acetoacetate ester are chemically bound to each atom of zirconium or hafnium and the remainder are "free".

Preferably, the complex is a complex of at least one of titanium and zirconium.

The preferred acetoacetate ester for preparing the complex is ethyl acetoacetate. The complex can be prepared from more than one acetoacetate ester but preferably only one acetoacetate ester is present in the complex.

Typically, the complexes of titanium, zirconium or hafnium are prepared from titanium, zirconium or hafnium alkoxides having the general formula $M(OR)_4$ in which M is Ti, Zr or Hf and R is a substituted or unsubstituted, cyclic or linear, alkyl, alkenyl, aryl or alkyl-aryl group or mixtures thereof. Preferably, R contains up to 8 carbon atoms and, more preferably, up to 6 carbon atoms.

Generally, all four OR groups will be identical but alkoxides derived from a mixture of alcohols can be used and mixtures of alkoxides can be employed when more than one metal is present in the complex. Suitable alkoxides include tetramethoxytitanium, tetra-ethoxytitanium, tetra-isopropoxytitanium, tetra-n-propoxytitanium, tetrabutoxytitanium, tetrakis(2-ethylhexoxy)titanium, tetrakis(2-ethoxyethoxy)titanium, tetracyclohexyloxytitanium, tetraphenoxy-titanium, tetrapropoxyzirconium, tetrabutoxyzirconium, tetra-n-propoxyhafnium and tetra-n-butoxyhafnium.

Alternatively, the complex can be prepared from condensed alkoxides of titanium, zirconium or hafnium. These compounds can be represented by the general formula $RO[M(OR)_2O]_xR$, wherein M and R have the same meaning as discussed above and x is an integer. Generally, these condensed alkoxides consist of a mixture containing compounds of the above formula with x having a range of values. Preferably, x has an average value in the range 2 to 16 and, more preferably, in the range 2 to 8. A condensed alkoxide is usually prepared by the controlled addition of water to an alkoxide, followed by removal of alcohol which is displaced. Suitable condensed alkoxides include the compounds known as polybutyl titanate, polybutyl zirconate and polyisopropyl titanate. Complexes of condensed alkoxides can also be prepared by forming a complex of an acetoacetate ester with an alkoxide, adding water to the complex and removing any by-product alcohol.

Other titanium, zirconium or hafnium compounds, such as titanium, zirconium or hafnium tetrachloride or alkoxides which have been substituted with, for example, glycol or phosphorus substituents can be used as raw materials for the formation of the complex used in the invention.

The complex can be readily prepared by mixing, for example, an alkoxide or condensed alkoxide with an appropriate amount of acetoacetate ester. Alcohol from the alkoxide will be displaced by the acetoacetate ester and, preferably, the displaced alcohol is removed by, for example, distillation. In a preferred method, 2 moles of acetoacetate ester per atom of Ti or 4 moles of acetoacetate ester per atom of Zr or Hf are added to an alkoxide or condensed alkoxide and the displaced alcohol is removed by distillation. Any additional acetoacetate ester required is then added to the stripped product. This method is advantageous because it provides a consistent product of known stoichiometry. It is possible to add all the acetoacetate ester in one charge and subsequently remove all the displaced alcohol but some of the "free" acetoacetate ester is usually accidentally removed during this process, leading to inconsistent products and contamination of the displaced alcohol.

Alternatively, when an organometallic composition according to the invention is used in a polyisocyanate composition, a product containing, for example, 2 moles of acetoacetate ester per Ti atom or 4 moles of acetoacetate ester per Zr or Hf atom can be prepared according to the method outlined above and this can be mixed with a polyisocyanate. Any additional acetoacetate ester required to produce the organometallic composition of the invention can be added to the polyisocyanate before or after the titanium, zirconium or hafnium compound has been added. This effectively results in the preparation of an organometallic composition according to this invention in situ in the polyisocyanate composition. Other methods of preparing the composition of the invention will be apparent to a person skilled in this art.

The organometallic complexes of the invention are particularly useful as curing agents in polyisocyanate compositions and compositions suitable for use with the organometallic compositions of the present invention may be any organic polyisocyanate compound or mixture of organic polyisocyanate compounds, provided said compounds have at least 2 isocyanate groups. Organic polyisocyanates include diisocyanates, particularly aromatic diisocyanates, and isocyanates of higher functionality.

Examples of organic polyisocyanates for which the organometallic complexes of the present invention are useful curing agents include aliphatic isocyanates such as hexamethylene diisocyanate; and aromatic isocyanates such as m- and p-phenylene diisocyanate, tolylene-2,4- and tolylene-2,6-diisocyanate, diphenylmethane-4,4'-diisocyanate, chlorophenylene-2,4-diisocyanate, naphthylene-1,5-diusocyanate, diphenylene-4,4'-diisocyanate, 4,4'-diisocyanate-3,3'-dimethyl-diphenyl, 3-methyldiphenylmethane-4,4'-di-isocyanate and diphenyl ether diisocyanate; and cycloaliphatic diisocyanates such as cyclohexane-2,4- and -2,3-diisocyanate, 1-methylcyclohexyl-2,4- and -2,6-diisocyanate and mixtures thereof and bis-(isocyanatocyclohexyl)methane and triisocyanates such as 2,4,6-triisocyanatotoluene and 2,4,4-triisocyanatodiphenylether.

Modified polyisocyanates containing isocyanurate, carbodiimide or uretonimine groups may be employed in conjunction with the organometallic complexes of the invention as well. Further blocked polyisocyanates, like the reaction product of a phenol or an oxime and a polyisocyanate, may be used, having a deblocking temperature below the temperature applied when using a polyisocyanate composition.

The organic polyisocyanate useful with the organometallic composition of the invention may also be an isocyanate-ended prepolymer made by reacting an excess of a diisocyanate or higher functionality polyisocyanate with a polyol.

Water-emulsifiable organic polyisocyanates like those described in UK patent no. 1 444 933, in European patent publication no. 516 361 and in PCT patent publication no. 91/03082 can also be used.

Mixtures of isocyanates may be used in conjunction with the organometallic composition of the invention, for example a mixture of tolylene diisocyanate isomers such as the commercially available mixtures of 2,4- and 2,6-isomers and also the mixture of di- and higher polyisocyanates. Polyisocyanate mixtures may optionally contain monofunctional isocyanates such as p-ethyl phenylisocyanate.

Such mixtures are well-known in the art and include the crude phosgenation products containing methylene bridged polyphenyl polyisocyanates, including diisocyanate, triisocyanate and higher polyisocyanates together with any phosgenation by-products.

Preferred isocyanates to be used in conjunction with the organometallic complexes of the present invention are those wherein the isocyanate is an aromatic diisocyanate or polyisocyanate of higher functionality such as a pure diphenylmethane diisocyanate or a mixture of methylene bridged polyphenyl polyisocyanates containing diisocyanates, triisocyanates and higher functionality polyisocyanates.

Methylene bridged polyphenyl polyisocyanates are well known in the art. They are prepared by phosgenation of corresponding mixtures of polyamines. For convenience, polymeric mixtures of methylene bridged polyphenyl polyisocyanates containing diisocyanate, triisocyanate and higher functionality polyisocyanates are referred to hereinafter as polymeric MDI. Polyisocyanates suitable for use with the organometallic complexes of the invention include SUPRASEC™ DNR, SUPRASEC™ 2185, RUBINATE™ M and RUBINATE™ 1840, all available from Imperial Chemical Industries.

Preferably the polyisocyanate is liquid at room temperature.

Conventional release agents can be added to or used in combination with a polyisocyanate composition containing a titanium, zirconium or hafnium complex of an acetoacetate ester according to the present invention.

In such compositions the conventional release agent is present in an amount varying between 0.2 and 10%, preferably between 0.5 and 6% and most preferably between 1 and 3% by weight based on the polyisocyanate whereas the titanium, zirconium or hafnium complex of an acetoacetate ester is preferably present in an amount varying between 0.2 and 4%, most preferably between 0.2 and 2% by weight based on the polyisocyanate.

Examples of conventional release agents include polysiloxanes, saturated or unsaturated fatty acids (such as oleic acid) or fatty acid amides or fatty acid esters and polyolefin waxes.

Preferred conventional release agents to be used in polyisocyanate compositions containing the organometallic complexes according to the present invention are polyolefin waxes or mixtures of polyolefin waxes, especially functionalised polyolefin waxes, which are dispersible in an aqueous medium to form an aqueous emulsion. More preferably, the polyolefin waxes are selected from oxidised polyethylene waxes and oxidised polypropylene waxes.

A preferred method for using the release agent is to apply the emulsion to the surface of the polyisocyanate treated lignocellulosic material or to the press metal surface prior to hot pressing the combination.

When used, an aqueous emulsion of the polyolefin wax should normally contain a sufficient amount of the polyolefin wax to provide a coverage of about 0.01 to about 1, and preferably about 0.02 to about 0.5 mg of the polyolefin wax per $cm^2$ of lignocellulosic material or press metal surface. Generally, lower levels of polyolefin wax are preferred as they are more cost effective. When taking the emulsifiers into account, the aqueous emulsions will usually contain about 0.2 to about 10%, preferably about 0.3 to about 5% by weight of total solids. The emulsions are usually prepared at 30 to 40% total solids, transported to the point of use and then diluted with water to the desired concentration.

It has been found that the polyolefin wax emulsion, when used in combination with polyisocyanate compositions containing organometallic compositions of the present invention, may be usefully applied to the lignocellulosic material or press metal surface in an amount equivalent to 8 to 14 mg per $cm^2$.

A particularly preferred polyethylene wax emulsion which can be used in a process in combination with an organometallic composition of the present invention in combination with a polyisocyanate is Rubilon™ 603 or Rubilon™ 605, both available from Imperial Chemical Industries.

A particularly preferred polypropylene wax emulsion which can be used in a process in combination with an organometallic composition of the present invention in combination with a polyisocyanate is ME 42040 available from Michelman Inc. of Cincinnati, Ohio.

In order to further improve the storage stability of a polyisocyanate composition containing an organometallic composition of the present invention a diluent may be added to the composition. Suitable diluents include plasticizers of the type mentioned in "Taschenbuch der Kunststoff-Additive", Ed. by R. Gachter and H. Muller, Carl Hanser Verlag Munchen, third edition, 1989. Preferred diluents are phthalates, aliphatic carboxylates, fatty acid esters, linseed oil and soybean oil. A particularly preferred diluent is Priolube 1403 available from Unichema being methyloleate. These diluents are added in amounts of from 1 to 40 parts by weight per 100 parts by weight of polyisocyanate and preferably in amounts of from 1 to 15 parts by weight per 100 parts by weight of polyisocyanate.

A composition containing an organometallic composition of the present invention and a polyisocyanate may further comprise conventional additives like flame retardants, lignocellulosic preserving agents, fungicides, waxes, sizing agents, fillers, surfactants, thixotropic agents and other binders like formaldehyde condensate adhesive resins and lignin (optionally in combination with a lignin solvent such as described in PCT Patent Application No. EP96/00924).

A particularly preferred additive to be used in a polyisocyanate composition containing an organometallic composition of the present invention is a coupling agent such as an organofunctional silane (for example, Dynasylan AMEO, available from Huels). Adding such a coupling agent to the polyisocyanate composition leads to improved board properties. The organofunctional silane coupling agents are used in amounts ranging from 0.01 to 3%, preferably from 0.1 to 2% by weight based on the polyisocyanate.

The organometallic composition of present invention can be used in a process for preparing lignocellulosic bodies by bringing lignocellulosic parts into contact with a polyisocyanate composition containing the organometallic composition of the present invention and pressing this combination.

A typical process comprises the steps of
a) bringing said lignocellulosic material in contact with a polyisocyanate composition containing an organometallic composition of the present invention and,
b) subsequently allowing said material to bind.

The lignocellulosic bodies are prepared by bringing the lignocellulosic parts into contact with a polyisocyanate composition by means such as mixing, spraying and/or spreading the composition with/onto the lignocellulosic parts and by pressing the combination of the polyisocyanate composition and the lignocellulosic parts, preferably by hot-pressing, normally at 150° C. to 250° C. and 2 to 6 MPa specific pressure.

Such binding processes are commonly known in the art.

In waferboard manufacture the lignocellulosic material and the polyisocyanate composition may be conveniently mixed by spraying the present polyisocyanate composition on the lignocellulosic material while it is being agitated.

As described hereinbefore, in a preferred process, a release agent, which is preferably an aqueous emulsion of a polyolefin wax, is applied to the surface of the polyisocyanate treated lignocellulosic material or to the press metal surface prior to hot pressing the combination.

The lignocellulosic material after treatment with the polyisocyanate composition containing an organometallic composition according to the invention is placed on caul plates made of aluminium or steel which serve to carry the furnish into the press where it is compressed to the desired extent usually at a temperature between 150° C. and 250° C.

While the process is particularly suitable for the manufacture of waferboard known extensively as oriented strand board and will be largely used for such manufacture, the process may not be regarded as limited in this respect and can also be used in the manufacture of medium density fibreboard, particle board (also known as chipboard) and plywood.

Thus the lignocellulosic material used can include wood strands, woodchips, wood fibres, shavings, veneers, wood wool, cork, bark, sawdust and like waste products of the wood working industry as well as other materials having a lignocellulosic basis such as paper, bagasse, straw, flax, sisal, hemp, rushes, reeds, rice hulls, husks, grass, nutshells and the like. Additionally, there may be mixed with the lignocellulosic materials other particulate or fibrous materials such as ground foam waste (for example, ground polyurethane foam waste), mineral fillers, glass fibre, mica, rubber, textile waste such as plastic fibres and fabrics.

When the polyisocyanate composition containing the organometallic composition of the invention is applied to the lignocellulosic material, the weight ratio of polyisocyanate/ lignocellulosic material will vary depending on the bulk density of the lignocellulosic material employed. Therefore, the polyisocyanate compositions may be applied in such amounts to give a weight ratio of polyisocyanate/ lignocellulosic material in the range of 0.1:99.9 to 20:80 and preferably in the range of 0.5:99.5 to 10:90.

If desired, other conventional binding agents, such as formaldehyde condensate adhesive resins, may be used in conjunction with the polyisocyanate composition containing the organometallic composition.

More detailed descriptions of methods of manufacturing waferboard and similar products based on lignocellulosic material are available in the prior art. The techniques and equipment conventionally used can be adapted for use with polyisocyanate compositions containing organometallic compositions of the resent invention.

Polyisocyanate compositions containing organometallic compositions of the present invention are extremely effective in minimising unwanted adhesion to caul plates, press plates and other surfaces with which the treated lignocellulosic material may come into contact. Their storage stability and release performance is improved compared to polyisocyanate compositions of the prior art, as well as the obtained board properties.

The sheets and moulded bodies produced from the polyisocyanate compositions containing organometallic compositions of the present invention have excellent mechanical properties and they may be used in any of the situations where such articles are customarily used.

The invention is illustrated but not limited by the following examples.

EXAMPLE 1

Preparation of Product A

A reactor was charged with tetraisopropyl titanate (1400 kg, Tilcom® TIPT from ICI Vertec). Ethylacetoacetate (1282 kg) was then added with stirring. The resulting product was a pale red liquid. The displaced alcohol (580 kg, isopropanol) was then removed by evaporation to leave a red liquid, PRODUCT A (2090 kg).

Product A was then diluted by addition of various amounts of methylacetoacetate, ethylacetoacetate and cetylacetoacetate in the following molar ratios.

TABLE 1

| Sample | Moles Product A | Moles Methylacetoacetate |
|---|---|---|
| Test 1 | 1 | 1.1 |
| Test 2 | 1 | 2.2 |
| Test 3 | 1 | 4.4 |
| Test 4 | 1 | 6.6 |
| Test 5 | 1 | 8.8 |
| Test 6 | 1 | 11 |

TABLE 2

| Sample | Moles Product A | Moles Ethylacetoacetate |
|---|---|---|
| Test 7 | 1 | 1.1 |
| Test 8 | 1 | 2.2 |
| Test 9 | 1 | 4.4 |
| Test 10 | 1 | 6.6 |
| Test 11 | 1 | 8.8 |
| Test 12 | 1 | 11 |

TABLE 3

| Sample | Moles Product A | Moles Cetylacetoacetate |
|---|---|---|
| Comparison 1 | 1 | 1.1 |
| Comparison 2 | 1 | 2.2 |
| Comparison 3 | 1 | 4.4 |
| Comparison 4 | 1 | 6.6 |
| Comparison 5 | 1 | 8.8 |
| Comparison 6 | 1 | 11 |

The products were evaluated by preparing a number of compositions comprising 100 parts by weight of polyisocyanate (polymeric MDI, SUPRASEC DNR, available from Imperial Chemical Industries) and various amounts of the samples designated Test 1 to 12 (see Table 4 below). Each composition contained the same concentration of Product A. The compositions were then stored at 45° C. and the viscosity tested by means of a Brookfield viscometer at various intervals.

TABLE 4

| Sample | Parts by weight | Parts by weight Suprasec DNR |
|---|---|---|
| Test 1 | 0.78 | 100 |
| Test 2 | 0.96 | 100 |
| Test 3 | 1.32 | 100 |
| Test 4 | 1.67 | 100 |
| Test 5 | 2.03 | 100 |
| Test 6 | 2.38 | 100 |
| Test 7 | 0.80 | 100 |
| Test 8 | 1.00 | 100 |
| Test 9 | 1.40 | 100 |
| Test 10 | 1.80 | 100 |
| Test 11 | 2.20 | 100 |
| Test 12 | 2.60 | 100 |

As a comparison a number of compositions comprising 100 parts by weight of polyisocyanate (polymeric MDI, SUPRASEC DNR, available from Imperial Chemical Industries) and various amounts of the samples designated Comparison 1 to 6 (see Table 5 below) were made up. All these compositions contained the same amount of Product A, this amount being the same as the amount of Product A in each of the compositions designated Test 1 to Test 12. These compositions were then stored at 45° C. and the viscosity tested using a Brookfield viscometer at the same intervals.

TABLE 5

| Sample | Parts by weight | Parts by weight Suprasec DNR |
|---|---|---|
| Comparison 1 | 1.1 | 100 |
| Comparison 2 | 1.6 | 100 |
| Comparison 3 | 2.6 | 100 |
| Comparison 4 | 3.6 | 100 |
| Comparison 5 | 4.6 | 100 |
| Comparison 6 | 5.6 | 100 |

The following results were obtained for the systems based on Product A with various added amounts of methylacetoacetate and ethylacetoacetate [all results are reported in Pa s].

TABLE 6

Product A + Methylacetoacetate

| Time (Days) | Test 1 | Test 2 | Test 3 | Test 4 | Test 5 | Test 6 |
|---|---|---|---|---|---|---|
| 0 | 0.292 | 0.288 | 0.274 | 0.272 | 0.267 | 0.267 |
| 14 | 0.828 | 0.548 | 0.632 | 0.678 | 0.746 | 0.806 |
| 25 | 1.208 | 0.734 | 0.840 | 1.007 | 1.078 | 1.153 |
| 30 | n.m. | 1.050 | 1.139 | 1.330 | 1.526 | 1.756 |
| 46 | 2.568 | 1.207 | 1.239 | 1.546 | 1.767 | 2.125 |
| 67 | n.m. | 1.917 | 1.707 | 2.209 | 2.579 | 3.392 | n.m. = not measured

TABLE 7

Product A + Ethylacetoacetate

| Time (Days) | Test 7 | Test 8 | Test 9 | Test 10 | Test 11 | Test 12 |
|---|---|---|---|---|---|---|
| 0 | 0.305 | 0.293 | 0.280 | 0.270 | 0.263 | 0.263 |
| 14 | 0.787 | 0.600 | 0.645 | 0.717 | 0.806 | 0.814 |
| 25 | 1.136 | 0.879 | 0.911 | 1.078 | 1.197 | 1.251 |
| 30 | n.m. | 1.137 | 1.225 | 1.538 | 1.734 | 1.811 |
| 46 | 2.486 | 1.310 | 1.410 | 1.735 | 2.240 | 2.018 |
| 67 | n.m. | 2.028 | 1.943 | 2.440 | 3.275 | 3.192 | n.m. = not measured

The following results were obtained for the systems based on Product A with various added amounts of cetylacetoacetate [all results reported in Pa s].

TABLE 8

Product A + Cetylacetoacetate

| Time (Days) | Comparison 1 | Comparison 2 | Comparison 3 | Comparison 4 | Comparison 5 | Comparison 6 |
|---|---|---|---|---|---|---|
| 0 | 0.324 | 0.296 | 0.296 | 0.277 | 0.279 | 0.264 |
| 14 | 1.195 | 0.599 | 0.627 | 0.630 | 0.667 | 0.626 |
| 25 | 1.995 | 0.797 | 0.839 | 0.851 | 1.014 | 0.989 |
| 30 | n.m. | 1.145 | 1.168 | 1.049 | 1.430 | 1.427 |
| 46 | 4.620 | 1.396 | 1.281 | 1.162 | 1.608 | 1.620 |
| 67 | n.m. | 2.443 | 1.853 | 1.610 | 2.260 | 2.309 | n.m. = not measured

Generally, the most relevant period for storage stability at room temperature is the period 14 to 46 days after production of a polyisocyanate composition. From Tables 6 to 8 above, it can be seen that the optimum (generally, lowest) viscosity after 46 days at 45° C. (an accelerated test) is achieved in Test 2 (2.2 moles methylacetoacetate), Test 8 (2.2 moles ethylacetoacetate) and Comparison 4 (6.6 moles cetylacetoacetate). The results demonstrate that the titanium complexes used in the composition of the invention provide a more economical means of stabilising the polyisocyanate composition.

EXAMPLE 2

Preparation of Product B

A flask was charged with tetra-n-propyl zirconate (43.7 g, Tilcom® NPZ [75% solution of $Zr(On—C_3H_7)_4$ in n-propanol] from ICI Vertec) and placed in a cold water bath. Methylacetoacetate (46.5 mg) was added over a period of one hour whilst the mixture was stirred. The resulting product was a pale yellow liquid. The displaced alcohol (35.3 g, n-propanol) was then removed on a rotary evaporator to leave a yellow oil (54.8 g). The oil was then mixed with additional methylacetoacetate (11.6 g) to yield PRODUCT B.

To evaluate the product a composition comprising 100 parts by weight of polyisocyanate (polymeric MDI, SUPRASEC DNR, available from Imperial Chemical Industries) and 2.09 parts by weight Product B was prepared in duplicate. The compositions were then stored at 45° C. and the viscosity tested at various intervals using a Brookfield viscometer. Results are reported in Table 9 below in Pa s.

TABLE 9

| Time (Days) | Product B(i) | Product B(ii) |
| --- | --- | --- |
| 0 | 0.220 | 0.220 |
| 20 | 0.440 | 0.400 |
| 41 | 0.580 | 0.520 |
| 62 | 0.660 | 0.640 |
| 84 | 1.020 | 1.340 |

Preparation of Product C

A flask was charged with tetra-n-propyl zirconate (43.7 g, Tilcom® NPZ [75% solution of $Zr(On—C_3H_7)_4$ in n-propanol] from ICI Vertec) and placed in a cold water bath. Methylacetoacetate (46.5 g) was added over a period of one hour whilst the mixture was stirred. The resulting product was a pale yellow liquid. The displaced alcohol (34.3 g, n-propanol) was then removed on a rotary evaporator to leave a yellow oil (55.8 g). The oil was then mixed with additional methylacetoacetate (23.2 g) to yield PRODUCT C.

To evaluate the product a composition comprising 100 parts by weight of polyisocyanate (polymeric MDI, SUPRASEC DNR, available from Imperial Chemical Industries) and 2.48 parts by weight Product C was prepared in duplicate. The compositions were then stored at 45° C. and the viscosity tested at various intervals using a Brookfield viscometer. Results are reported in Table 10 below in Pa s.

TABLE 10

| Time (Days) | Product C(i) | Product C(ii) |
| --- | --- | --- |
| 0 | 0.220 | 0.220 |
| 20 | 0.460 | 0.500 |
| 41 | 0.500 | 0.500 |
| 62 | 0.720 | 0.620 |
| 84 | 1.280 | 0.980 |

Preparation of Product D

A flask was charged with tetra-n-propyl zirconate (87.3 g, Tilcom® NPZ [75% solution of $Zr(On—C_3H_7)_4$ in n-propanol) from ICI Vertec) and placed in a cold water bath. Ethylacetoacetate (104 g) was added over a period of one hour whilst the mixture was stirred. The resulting product was a pale yellow liquid. The displaced alcohol (67.1 g, n-propanol) was then removed on a rotary evaporator to leave a yellow oil (124.3 g). The oil was then mixed with additional ethyl acetoacetate (26 g) to yield PRODUCT D.

To evaluate the product a composition comprising 100 parts by weight of polyisocyanate (polymeric MDI, SUPRASEC DNR, available from Imperial Chemical Industries) and 2.21 parts by weight Product D was prepared in duplicate. The compositions were then stored at 45° C. and the viscosity of the compositions tested at various intervals using a Brookfield viscometer. Results are reported in Table 11 below in Pa s.

TABLE 11

| Time (Days) | Product D(i) | Product D(ii) |
| --- | --- | --- |
| 0 | 0.220 | 0.220 |
| 20 | 0.480 | 0.460 |
| 41 | 0.540 | 0.560 |
| 62 | 0.700 | 0.920 |
| 84 | 1.140 | 1.040 |

Preparation of Product E

A flask was charged with tetra-n-propyl zirconate (87.3 g, Tilcom® NPZ [75% solution of $Zr(On—C_3H_7)_4$ in n-propanol] from ICI Vertec) and placed in a cold water bath. Ethylacetoacetate (104 g) was added over a period of one hour whilst the mixture was stirred. The resulting product was a pale yellow liquid. The displaced alcohol (70.0 g, n-propanol) was then removed on a rotary evaporator to leave a yellow oil (121.4 g). The oil was then mixed with additional ethylacetoacetate (52 g) to yield PRODUCT E.

To evaluate the product a composition comprising 100 parts by weight of polyisocyanate (polymeric MDI, SUPRASEC DNR, available from Imperial Chemical Industries) and 2.56 parts by weight Product E was prepared in duplicate. The compositions were then stored at 45° C. and the viscosity of the compositions tested at various intervals using a Brookfield viscometer. Results are reported in Table 12 below in Pa s.

TABLE 12

| Time (Days) | Product E(i) | Product E(ii) |
| --- | --- | --- |
| 0 | 0.220 | 0.220 |
| 20 | 0.560 | 0.580 |
| 41 | 0.620 | 0.600 |
| 62 | 0.860 | 0.780 |
| 84 | 1.060 | 0.960 |

The zirconium complexes (Products B, C, D E) show improved stability over a longer period of time than the titanium complexes of Comparison 1 to 6 (Table 8).

EXAMPLE 3

Preparation of Product F

A flask was charged with tetraisopropyl titanate (71 g, Tilcom® TIPT from ICI Vertec) and placed in a cold water bath. Ethylacetoacetate (65 g) was added over a period of one hour whilst the mixture was stirred. Following addition of ethylacetoacetate, distilled water (1.1 g, 0.25 moles per mole Ti) was added to the mixture with thorough stirring. The resulting product was a pale red liquid. The displaced alcohol (43.4 g, isopropanol) was then removed on a rotary evaporator to leave a red liquid (94.5 g). This liquid was then mixed with additional ethyl acetoacetate (65 g) to yield PRODUCT F.

To evaluate the product a composition comprising 100 parts by weight of polyisocyanate (polymeric MDI, SUPRASEC DNR, available from Imperial Chemical Industries) and 0.88 parts by weight Product F was prepared. The composition was then stored at 45° C. and the viscosity of the composition tested at various intervals using a Brookfield viscometer.

Preparation of Product G

A flask was charged with tetraisopropyl titanate (71 g, Tilcom® TIPT from ICI Vertec) and placed in a cold water bath. Ethylacetoacetate (65 g) was added over a period of one hour whilst the mixture was stirred. Following addition of ethylacetoacetate, distilled water (2.3 g, 0.5 moles per mole of Ti) was added to the mixture with thorough stirring. The resulting product was a pale red liquid. The displaced alcohol (48.4 g, isopropanol) was then removed on a rotary evaporator to leave a red liquid (93.3 g). This liquid was then mixed with additional ethyl acetoacetate (65 g) to yield PRODUCT G.

To evaluate the product a composition comprising 100 parts by weight of polyisocyanate (polymeric MDI, SUPRASEC DNR, available from Imperial Chemical Industries) and 0.88 parts by weight Product G was prepared. The composition was then stored at 45° C. and the viscosity of the composition tested at various intervals using a Brookfield viscometer. Results are reported for Product F and Product G in Table 13 below in Pa s.

TABLE 13

| Time (Days) | Product F | Product G |
| --- | --- | --- |
| 0 | 0.220 | 0.220 |
| 10 | 0.455 | 0.520 |
| 40 | 0.760 | 0.760 |
| 60 | 1.100 | 1.200 |
| 80 | 1.140 | 1.220 |

EXAMPLE 4

A flask was charged with tetraisopropyl titanate (71 g, Tilcom® TIPT from ICI Vertec) and placed in a cold water bath. tert-Butylacetoacetate (79.1 g) was added over a period of one hour whilst the mixture was stirred. The resulting product was a pale yellow liquid. The displaced alcohol (30.0 g, isopropanol) was then removed on a rotary evaporator to leave a red liquid (120.0 g). This liquid was then mixed with additional ethyl acetoacetate (65 g) to yield PRODUCT H.

To evaluate the product a composition comprising 100 parts by weight of polyisocyanate (polymeric MDI, SUPRASEC DNR, available from Imperial Chemical Industries) and 1.02 parts by weight Product H was prepared. The composition was then stored at 45° C. and the viscosity of the composition tested at various intervals using a Brookfield viscometer. Results are reported in Table 14 below in Pa s.

TABLE 14

| Time (Days) | Viscosity |
| --- | --- |
| 0 | 0.220 |
| 10 | 0.480 |
| 40 | 1.160 |
| 60 | 1.800 |
| 80 | 2.160 |

EXAMPLE 5

Preparation of Product I

A flask was charged with tetraisopropyl titanate (71 g, Tilcom® TIPT from ICI Vertec) and placed in a cold water bath. Ethylacetoacetate (65 g) was added over a period of one hour whilst the mixture was stirred. Following addition of ethylacetoacetate, butyl acid phosphate (11.4 g, 0.25 moles) was added to the mixture with thorough stirring. The resulting product was a pale red liquid. The displaced alcohol (38.2 g, isopropanol) was then removed on a rotary evaporator to leave a red liquid (109.2 g). This liquid was then mixed with additional ethyl acetoacetate (65 g) to yield PRODUCT I.

To evaluate the product a composition comprising 100 parts by weight of polyisocyanate (polymeric MDI, SUPRASEC DNR, available from Imperial Chemical Industries) and 0.97 parts by weight Product I was prepared in duplicate. The compositions were then stored at 45° C. and the viscosity of the compositions tested at various intervals using a Brookfield viscometer (see Table 15).

Preparation of Product J

A flask was charged with tetraisopropyl titanate (71 g, Tilcom® TIPT from ICI Vertec) and placed in a cold water bath. Ethylacetoacetate (65 g) was added over a period of one hour whilst the mixture was stirred. Following addition of ethylacetoacetate, butyl acid phosphate (22.8 g, 0.5 moles) was added to the mixture with thorough stirring. The resulting product was a pale red liquid. The displaced alcohol (40.8 g, isopropanol) was then removed on a rotary evaporator to leave a red liquid (118.0 g). This liquid was then mixed with additional ethyl acetoacetate (65 g) to yield PRODUCT J.

To evaluate the product a composition comprising 100 parts by weight of polyisocyanate (polymeric MDI, SUPRASEC DNR, available from Imperial Chemical Industries) and 1.02 parts by weight Product J was prepared. The composition was then stored at 45° C. and the viscosity of the composition tested at various intervals using a Brookfield viscometer. Results are reported for Product I and Product J in Table 15 below in Pa s.

TABLE 15

| Time (Days) | Product I | Product J |
| --- | --- | --- |
| 0 | 0.220 | 0.220 |
| 10 | 0.440 | 0.389 |
| 40 | 0.880 | 0.580 |
| 60 | 1.320 | 0.960 |
| 80 | 1.360 | 1.040 |

What is claimed is:

1. An organometallic composition comprising
(a) at least one metal wherein said metal is selected from the group consisting of titanium, zirconium and hafnium and;

(b) an acetoacetate ester wherein said ester is an ester of an alcohol containing 1 to 6 carbon atoms;

wherein the molar ratio of Ti to acetoacetate ester is in the range 1:2.5 to 1:10 or the molar ratio of Zr or Hf to acetoacetate ester is in the range 1:4.5 to 1:10.

2. An organometallic composition according to claim 1 wherein the molar ratio of Ti to acetoacetate ester is in the range 1:2.5 to 1:8.

3. An organometallic composition according to claim 2 wherein the molar ratio of Ti to acetoacetate ester is in the range 1:3 to 1:6.

4. An organometallic composition according to claim 1 wherein the molar ratio of Zr or Hf to acetoacetate ester is in the range 1:4.5 to 1:8.

5. An organometallic composition according to claim 1 wherein the acetoacetate ester is ethyl acetoacetate.

6. An organometallic composition according to claim 1 wherein the composition has been prepared from a titanium, zirconium or hafnium alkoxide having the general formula $M(OR)_4$ wherein M is Ti, Zr or Hf and R is a subsituted or unsubstituted, cyclic or linear, alkyl, alkenyl, aryl or alkyl-aryl group.

7. An organometallic composition according to claim 6 wherein R contains up to 6 carbon atoms.

8. An organometallic composition according to claim 1 wherein said composition has been prepared from a condensed titanium, zirconium or hafnium alkoxide having the general formula $RO[M(OR)_2O]_xR$ wherein M is Ti, Zr or Hf, x is an integer and R is a substituted or unsubstituted, cyclic or linear, alkyl, alkenyl, aryl or alkyl-aryl group.

9. An organometallic composition according to claim 8 wherein the average value of x is in the range 2 to 16.

10. An organometallic composition according to claim 1 wherein said composition is prepared from an alkoxide or condensed alkoxide and displaced alcohol is removed.

11. An organometallic composition according to claim 1 wherein at least a portion of said metal and a portion of said acetoacetate ester form a complex.

* * * * *